(12) United States Patent
Takata et al.

(10) Patent No.: US 7,879,370 B2
(45) Date of Patent: Feb. 1, 2011

(54) COMPOSITION OF WHICH CHIEF INGREDIENT IS POLYSACCHARIDES HAVING AN IMMUNOREGULATORY FUNCTION

(75) Inventors: Ryoji Takata, Hiratsuka (JP); Reiko Yamamoto, Sagamihara (JP); Takaaki Yanai, Fujisawa (JP); Tomonori Kon-No, Yokohama (JP)

(73) Assignee: Merican Corporation, Tokyo (JP)

( * ) Notice: Subject to any disclaimer, the term of this patent is extended or adjusted under 35 U.S.C. 154(b) by 77 days.

(21) Appl. No.: 12/226,671

(22) PCT Filed: Apr. 4, 2007

(86) PCT No.: PCT/JP2007/058591

§ 371 (c)(1),
(2), (4) Date: Feb. 9, 2009

(87) PCT Pub. No.: WO2007/125823

PCT Pub. Date: Nov. 8, 2007

(65) Prior Publication Data

US 2009/0220531 A1      Sep. 3, 2009

(30) Foreign Application Priority Data

Apr. 26, 2006  (JP) .............................. 2006-121492
Oct. 20, 2006  (JP) .............................. 2006-286171

(51) Int. Cl.
*A01N 65/00* (2009.01)
(52) U.S. Cl. ...................................................... 424/725
(58) Field of Classification Search ....................... None
See application file for complete search history.

(56) References Cited

FOREIGN PATENT DOCUMENTS

| | | |
|---|---|---|
| JP | 59-11302 A | 1/1984 |
| JP | 02-215721 A | 8/1990 |
| JP | 02-248401 A | 10/1990 |
| JP | 02-255094 A | 10/1990 |
| JP | 2004-107660 A | 4/2004 |
| JP | 2006-137712 | 6/2006 |
| JP | 2006-213655 A | 8/2006 |
| SU | 1015883  * | 5/1983 |

OTHER PUBLICATIONS

Takata et al., Biosci. Biotechnol. Biochem., 69, (11), 2042-2050, 2005.*

* cited by examiner

*Primary Examiner*—Michael V Meller
(74) *Attorney, Agent, or Firm*—Jacobson Holman PLLC

(57) ABSTRACT

An object is to establish a method of preparation of novel polysaccharides from a cassis polysaccharide (CAPS), wherein the novel polysaccharides exhibit a higher immunoregulatory effect per unit amount, have a low viscosity, and can be handled readily during the method of preparation a final product. Another object is to provide health foods and drinks having high safety and an excellent immunoregulatory effect at a low cost by utilizing a juice, processed juice or a purified product. The present invention relates to a composition of which chief ingredient is novel polysaccharides, having an average molecular weight falling within a range of 10,000 to 40,000; which is obtained by partially digestion of CAPS with enzyme, and an immunoregulatory foods and drinks utilizing the composition.

12 Claims, 7 Drawing Sheets

US 7,879,370 B2

COMPOSITION OF WHICH CHIEF INGREDIENT IS POLYSACCHARIDES HAVING AN IMMUNOREGULATORY FUNCTION

This is 371 of PCT/JP2007/058591 filed Apr. 20, 2007.

TECHNICAL FIELD

The present invention relates to a novel composition of which chief ingredient is polysaccharides, that can be obtained by definitive partial degradation with enzymes of the polysaccharide fraction contained in black currant juice. The present invention further relates to an immunoregulator, containing this composition, having an immunoregulatory effect such as an antitumor effect or antiallergic effect, and to foods and drinks containing this composition. The composition has much higher immunoregulatory activity per unit quantity than the polysaccharides derived from conventional black currant juice, and due to its extremely low viscosity, is easy to handle in the preparation of products.

BACKGROUND ART

There is no end to international interest in food and health. This growing interest has also spread to the domains of food and immunity. Abnormal immunomechanisms are the causes of such obstinate modern diseases as allergies such as hay fever, infectious diseases, and cancer. Additionally, in contemporary Japan, an extended economic downturn, irregular lifestyles, poor eating habits, mental stress, and the like are widespread causes of damage to immunomechanisms. Meanwhile, the prevention of such obsinate diseases has become possible through foods (ingredients). In particular, in Japan, where fewer children and an increasing average age are the trends, it is easy to imagine how future medical expenses could drain national coffers, and the concept of preventive medicine is assuming ever greater significance.

Immunoresponses can be divided into innate immunity and acquired (adaptive) immunity. Innate immunity, the former, refers to the immune system with which we are equipped at birth. Typical cellular factors responsible for organic defense mechanisms include phagocytes such as neutrocytes, macrophages, and dendritic cells. These cells identify, rapidly engage, and eliminate foreign bodies, such as microorganisms, with the help of fluid factors such as complements and lectins. Innate immunity not only plays a role in the early prevention of infection, but also plays a role in subsequent early induced reactions and differentiation of later-stage acquired (adaptive) immunity. That is, innate immunity plays an important role in orientation of the balance between cellular immunity and humoral immunity.

Cellular immunity of which main players are cytotoxic T cells (also known as "killer T kills"), macrophages, and the like, primarily function to prevent intercellular infection such as viral infection and the tumors caused by such infection. Humoral immunity controls the class switch of IgG1 and IgE antibodies in B cells, functioning to prevent infection by microorganisms that primarily proliferate in outside cells, such as protozoa, fungi, parasites, mycoplasma, pneumococci, and *Escherichia coli*.

Cellular immunity and humoral immunity can be compared to the balancing of a seesaw. When this balance is disrupted for some reason (endogenous or exogenous), tipping toward cellular immunity, one becomes subject to autoimmune diseases such as insulin-dependent diabetes and chronic rheumatoid arthritis. Conversely, it has recently become clear that when this balance tips toward humoral immunity, various allergic disorders and cancer occur. That is, keeping these immunomechanisms well balanced is essential for maintaining bodily homeostasis.

Materials for food and drinks that regulate the balance of immunomechanisms in a normal state include those derived from fungi typified by mushrooms, yeasts and lactic acid bacteria, as well as seaweed, herbs, and the like (see Non-patent Documents 1 to 7). These are called as biological response modifiers (BRMs), meaning that they have a regulatory effect.

The present inventors focused on fruit, a material that is readily available, inexpensive, and considered safe by consumers, and discovered that a fraction of which chief ingredient is polysaccharides contained in black currant juice activated macrophages in vitro (see Patent Document 1). Next, they discovered that it had a strong antitumor effect in mouse antitumor tests conducted in vivo, and named this polysaccharide fraction cassis polysaccharide (CAPS) (see Non-patent Document 8).

[Non-Patent Document 1] Medical mushrooms as a source of antitumor and immunomodulating polysaccharides. (Appl. Microbiol. Biotechnol., 60, 258-274 (2002))

[Non-Patent Document 2] Antitumor activity and immune response of Mekabu fucoidan extracted from *Sporophyll of Undaria pinnatifida*. (In Vivo, 17, 245-250 (2003))

[Non-Patent Document 3] Antitumor potential of a polysaccharide-rich substance from the fruit juice of *Morinda citrifolia* (Noni) on Sarcoma 180 ascites tumour in mice. (Phytother. Res., 17, 1158-1164 (2003))

[Non-Patent Document 4] A polysaccharide, extract from *Grifola frondosa*, induces Th-1 dominant responses in carcinoma-bearing BALB/c mice. (Jpn. J. Pharmacol., 90, 357-360 (2002))

[Non-Patent Document 5] The anti-allergic effects of lactic acid bacteria are strain dependent and mediated by effects on both Th1/Th2 cytokine expression and balance. (Int. Arch. Allergy Immunol., 135, 205-215 (2004))

[Non-Patent Document 6] In vitro and in vivo anti-allergic activity of soy sauce. (Int. J. Mol. Med., 14, 879-884 (2004))

[Non-Patent Document 7] Clinical effects of Lactobacillus acidophilus strain L-92 on perennial allergic rhinitis: a double-blind, placebo-controlled study. (J. Dairy Sci., 88, 527-533 (2005))

[Non-Patent Document 8] Immunostimulatory Effects of a Polysaccharide-Rich Substance with Antitumor Activity Isolated from Black Currant (*Ribes nigrum* L.). (Biosci. Biotechnol. Biochem., 69 (11), 2042-2050 (2005))

[Patent Document 1] Japanese Unexamined Patent Publication (KOKAI) No. 2004-107660.

What is known in English as the "black currant" is known in Japanese as the "kurofusasuguri." It is widely grown primarily in North America, Europe, and more recently, New Zealand. It is a material that is extremely well known, particularly in the liquor and confectionery industry.

However, the black currant juice that is the starting material for CAPS is more expensive than the juice of the common fruit. Thus, the actual development of products has been impeded by high cost and the fact that black currant juice is highly viscous, making it hard to handle.

Accordingly, an object of the present invention is to inexpensively provide a novel material derived from black currant juice that has a good antitumor effect similar to that of CAPS, is of low viscosity, and is easy to handle.

That is, an object of the present invention is to more inexpensively provide a material having good physiological activity by providing a material having greater physiological activity than CAPS in the form of a novel substance derived from black currant juice.

A further object of the present invention is to provide inexpensive and safe foods and drinks, particularly health foods and drinks, using the above novel material having good physiological activity.

DISCLOSURE OF THE INVENTION

To solve the above-stated problems, the present inventors conducted a wide range of investigation, resulting in the discovery that a substance having an average molecular weight of about 10,000 to 40,000 produced by definitive partial enzymatic degradation of CAPS exhibited a higher immunoregulatory effect than CAPS while having a lower viscosity than CAPS. The present invention was devised on the basis of this discovery.

That is, the present invention is as set forth below:

[1] A composition of which chief ingredient is polysaccharides, having properties (1) to (3) below:

(1) an average molecular weight falling within a range of 10,000 to 40,000;

(2) rhamnose, mannose, arabinose, galactose, xylose, and glucose being comprised as neutral sugars; and (3) a molar ratio of the neutral sugars listed in (2) in the fraction having a molecular weight of 1,000 or greater being 18:3:19:30:1:29.

[2] The composition in accordance with [1], further having property (4) below:

(4) readily soluble in water and in 0 to 20 percent (v/v) ethanol aqueous solutions.

[3] The composition in accordance with [1] or [2] wherein the average molecular weight of said polysaccharides is about 20,000.

[4] The composition in accordance with any one of [1] to [3], only rhamnose, mannose, arabinose, galactose, xylose, and glucose are comprised as the neutral sugars.

[5] The composition in accordance with any one of [1] to [4], further comprising protein and a polyphenol compound.

[6] The composition in accordance with any one of [1] to [5], obtained by partially digesting black current juice or a polysaccharide-containing fraction separated from black currant juice with β(beta)-galactosidase.

[7] A method for preparing a composition of which chief ingredient is polysaccharides by partially digesting black currant juice or a polysaccharide-containing fraction separated from black currant juice with β(beta)-galactosidase until the average molecular weight of the polysaccharides falls within a range of 10,000 to 40,000.

[8] The preparing method in accordance with [7], wherein said composition of which chief ingredient is polysaccharides is the composition in accordance with any one of [1] to [5].

[9] An immunoregulator comprising the composition in accordance with any one of [1] to [6], or the composition obtained by the preparing method in accordance with [7] or [8].

[10] The immunoregulator in accordance with [9], having an antitumor effect and/or an antiallergic effect.

[11] The immunoregulator in accordance with [9] or [10], having a hay fever-suppressing effect.

[12] A beverage or food comprising the composition in accordance with any one of [1] to [6] or a composition obtained by the preparing method in accordance with [7] or [8].

The present invention provides a novel composition of which chief ingredient is polysaccharides from isolated CAPS or black currant juice, that has a higher immunoregulatory effect per unit quantity and lower viscosity, while affording ease of handling in the process of preparing a final product. This composition exhibits a higher immunoregulatory effect than conventional CAPS. An immunoregulator and health foods and drinks exhibiting immunoregulatory effects such as an antitumor effect and antiallergic effect that comprise this composition as an active ingredient are also provided. In particular, an immunoregulator and health foods and drinks comprising this composition as active ingredient and exhibiting a hay fever-suppressing effect are also provided. Since the composition of the present invention is processed from black currant juice, an item that is consumed on a daily basis, it has no negative effect on the human body with long-term consumption.

According to the present invention, a method for preparing the above composition by the direct enzymatic treatment of black currant juice is provided. The viscosity of the juice obtained by this method decreases considerably in the course of treatment, affording the advantage of ready handling of the juice in product preparing.

BEST MODES OF CARRYING OUT THE INVENTION

Composition of which Chief Ingredient is Polysaccharides and Method for Preparing Same The composition of which chief ingredient is polysaccharides of the present invention can be obtained by definitive partial enzymatic degradation of CAPS separated from black currant juice or from black currant juice itself.

A method of preparing a polysaccharide-containing composition from CAPS separated from black currant juice will be described first.

CAPS can be prepared from black currant juice by the methods described in Japanese Unexamined Patent Publication (KOKAI) No. 2004-107660 (Patent Document 1) and Nonpatent Document 8. Briefly, black currant juice (the centrifugation supernatant of black currant puree) is passed through cation exchange resin and anion exchange resin to remove various ionic substances. Next, the juice is passed through a C-18 reverse phase column to remove polyphenol compounds. The fraction obtained by passing through is dialyzed with pure water and freeze-dried to obtain CAPS.

In the definitive partial degradation of CAPS, β(beta)-galactosidase is added to the CAPS. The quantity of β(beta)-galactosidase added can be suitably determined based on the concentration of CAPS in the reaction solution, the pH, the reaction temperature, the reaction time, and the source and degree of purity of the β(beta)-galactosidase. When the quantity is excessively small, the reaction requires an excessively long period. In some cases, the enzyme deactivates along the way, making it impossible to obtain a degradation product of desired molecular weight. Conversely, when the quantity is excessively large, the reaction progresses too fast, making it difficult to halt the reaction at a suitable time and sometimes increasing the cost of product preparing. Taking such factors into account, when the β(beta)-galactosidase is in the form of a high purity preparation (reagent grade), for example, the addition of a quantity (range) of β(beta)-galactosidase of about 0.01 to 1 percent (w/v), desirably 0.05 to 0.5 percent (w/v) is suitable. When the purity of the β(beta)-galactosidase preparation is poor, as in the case of a food processing-use enzyme, for example, a quantity of about 0.2 to 2 percent (w/v) is suitable. However, the quantity (range) of β(beta)-galactosidase added is given here merely by way of example, and can be suitably determined based on the conditions set forth above.

The β(beta)-galactosidase employed is ideally derived from *Aspergillus oryzae*. However, β(beta)-galactosidase of other derivation can also be employed. Examples of β(beta)-galactosidase of other derivation that is suitable for use is β(beta)-galactosidase derived from *Kluyveromyces lactis, Saccharomyces fagilis*, and *Escherchia coli*.

In enzymatic treatment, the peaks on the side of sugars (monosaccharides to oligosaccharides) with molecular weights of about 1,000 or lower is ignored. When the peaks on the polysaccharide side (MW>1,000) fall within a molecular weight range of about 10,000 to 40,000, the enzymatic reaction is halted to obtain the desired composition containing polysaccharides. In this process, for example, portions of the reaction solution can be sampled over time from the start of the reaction, gel filtration analysis by high-performance liquid chromatography (HPLC) can be conducted, and the time for halting the reaction can be monitored. A differential refractometer can be employed as the detector in high-performance liquid chromatography to essentially detect only sugars (monosaccharides, disaccharides, oligosaccharides, and polysaccharides). The enzymatic reaction can be conducted at close to the optimal temperature of the enzyme (for example, about 50° C.). Due to the high thermal stability of the polysaccharides produced, the enzymatic reaction can be halted by deactivating the enzyme for several minutes by, for example, boiling for 5 to 10 minutes.

After deactivating the enzyme, the product can be purified as needed to obtain the composition of the present invention principally comprising polysaccharides. The purification method is not specifically limited. For example, the small quantity of insoluble precipitates produced by boiling can be removed by centrifugation. After removing the insoluble precipitates, ultrafiltration of the fraction having a molecular weight of 1,000 can be used to remove molecules with a low molecular weight of 1,000 or less (monosaccharides to polysaccharides). As needed, freeze drying can also be used to obtain the composition of the present invention of which chief ingredient is polysaccharides.

The physicochemical properties of the polysaccharides contained in the composition of which chief ingredient is polysaccharides of the present invention (also referred to as "the present polysaccharides" hereinafter) that is finally obtained by purification are given in (1) to (4) below.

(1) Molecular Weight:
The average molecular weight is about 10,000 to 40,000, desirably about 15,000 to 25,000, preferably about 20,000. The average molecular weight is based on gel filtration analysis by HPLC.

(2) Sugar Composition:
When the neutral sugar composition is examined by HPLC following hydrochloric acid hydrolysis, it is comprised only of rhamnose, mannose, arabinose, galactose, xylose, and glucose.

(3) The molar ratio of the neutral sugars rhamnose, mannose, arabinose, galactose, xylose, and glucose in the fraction with a molecular weight of 1,000 and greater is about 18:3:19:30:1:29. No physiological activity (cytokine-inducing activity such as TNF-α(alpha)) is observed in assay systems in vitro in monosaccharides to oligosaccharides with a molecular weight of 1,000 or lower.

(4) Solubility:
Readily soluble in water and 0 to 20 percent (v/v) ethanol aqueous solutions.

The polysaccharides contained in the composition of the present invention can also have the physicochemical properties of (5) and (6) below.

(5) Thermal Stability
When heat treated at 100° C. for 10 minutes, the physiological activity of the present polysaccharides (cytokine-inducing activity in macrophages) was not deactivated.

(6) Color-Forming Reaction:
The polysaccharides are positive for color reactions by the phenol-sulfuric acid method and carbazol-sulfuric acid method.

The composition of the present invention of which chief ingredient is the above polysaccharides can also have the physicochemical properties of (7) to (9) below.

(7) Infrared Absorption Spectrum:
FIG. 1 shows a chart of the infrared radiation absorption spectrum of the polysaccharides (MW>1,000) purified and freeze-dried. Maximum absorption was observed in the vicinity of 1,000 $cm^{-1}$.

(8) Absorption Spectrum:
FIG. 2 shows a chart of the absorption spectrum of the saccharides (dissolved in pure water to a concentration of 80 microgram/mL). Maximum absorption was observed at 194 nm.

(9) Color Characteristics:
When the present polysaccharides were freeze-dried after dialysis in pure water, the resulted exhibited a pale brown color.

The content of the polysaccharides contained in the composition of which chief ingredient is polysaccharides of the present invention obtained by purification falls within a range, for example, of from 50 to 95 mass percent, desirably within a range from 60 to 95 mass percent, and preferably, within a range from 80 to 95 mass percent.

The composition of the present invention contains protein and polyphenol compounds in addition to polysaccharides. The content of the protein and polyphenol compounds desirably ranges from 0 to 5 mass percent and from 5 to 45 mass percent, respectively.

The method for directly preparing the composition of which chief ingredient is the above polysaccharides from black currant juice will be described next.

The black currant juice employed can be either a puree containing all the components of the black currant fruit, or the juice from which insoluble components derived primarily from the peel, seeds, and the like have been removed in advance by pretreatment in the form of centrifugal processing, for example.

As set forth above, the enzyme employed is ideally β(beta)-galactosidase derived from *Aspergillus oryzae*. However, as also set forth above, β(beta)-galactosidase of other derivation can also be employed. The quantity of β(beta)-galactosidase added can be suitably determined by taking into account the same factors as for the definitive partial degradation of CAPS set forth above. For example, for a β(beta)-galactosidase preparation of high purity (reagent grade), about 0.01 to 1 percent (w/v), desirably 0.05 to 0.5 percent (w/v), is suitable. For a β(beta)-galactosidase preparation of low purity, such as a food processing-use enzyme, about 0.2 to 2 percent (w/v) is suitable.

To retain the flavor of black currant, a reaction in which enzymatic treatment, deactivation, and sterilization conditions are made as mild as possible is desirable. For example, enzymatic treatment can be conducted in a reaction at in the vicinity of 40° C. that is close to physiological conditions. The pH of black currant juice, at about 2.9, is extremely low, so a lower reaction temperature is desirably employed than for enzymatic degradation of separated or partially purified CAPS. Portions of the reaction solution can be sampled over time from the start of the enzymatic reaction and gel filtration based on high-performance liquid chromatography (HPLC) employing a detector in the form of a differential refractometer can be used to determine when to halt the reaction. Peaks on the side of sugars having a molecular weight of about 1,000 or less (monosaccharides to oligosaccharides) are ignored. When the peaks on the polysaccharide side (MW>1,000) indicate an average molecular weight of about 20,000, the reaction is halted by means of a deactivation operation. Due to the extremely low 2.9 pH of black currants, the enzyme is deactivated by being maintained at in the vicinity of 70° C. for several minutes. This operation can also be used for sterilization.

The above operation yields a composition of which chief ingredient is polysaccharides from black currant juice. Enzymatic treatment reduces the viscosity of the black currant juice to about ⅓ the level prior to enzymatic treatment, although this also depends on the degree of degradation. Accordingly, the product affords the physical property of being extremely easy to handle.

The content of polysaccharides in the composition of which chief ingredient is polysaccharides of the present invention that is obtained from black currant juice falls within a range of 50 to 95 mass percent.

The composition of the present invention obtained from black currant juice further contains protein and polyphenol compounds in addition to polysaccharides. The content of protein and that of polyphenol compounds ranges from 0 to 5 mass percent and 5 to 45 mass percent, respectively.

[The Immunoregulator and Food and Drink Products]

The present invention includes immunoregulators and food and drink products containing the composition of which chief ingredient is polysaccharides of the present invention. The composition containing polysaccharide ingredients newly produced from polysaccharides (principal component: CAPS) contained in the fruit of the black currant has an immunoregulatory effect accompanying an antitumor effect, antiallergic effect, and the like. In particular, the above-described composition of the present invention has a hay fever-suppressing effect and can be employed as an immunoregulator. The fact that the above-described composition of the present invention has a suppressive effect on Japanese cedar hay fever symptoms in humans is specifically indicated in examples described further below.

The above immunoregulator is obtained by admixing various materials to the composition containing polysaccharides (CAPS) derived from black currant fruit, removing moisture from this mixture by spray drying or freeze drying, and physically mixing the dry powder obtained with an excipient and granulating the mixture to prepare a powder or granular composition. Examples of the above-mentioned various materials that can be employed are sweeteners, coloring materials, storage stabilizers, oxidation-inhibiting agents, acidifiers, fragrance materials, bitterness-imparting materials, spices, and flavoring agents. Examples of the excipient which can be used are lactose, crystalline cellulose, starch (dextrin), sucrose fatty acid esters, glycerin fatty acid esters and the like.

In general, the immunoregulator of the present invention is orally administered. The dosage administered is determined based on the patient's symptoms, age, body weight, and the like according to a physician's prescription. The usual range of the dosage administered is, for example, 0.1 g to 100 g. A single administration or multiple separated administrations can be employed.

Food and drink products containing the composition of which chief ingredient is polysaccharides of the present invention can also be employed to regulate immune strength.

The above food and drink products of the present invention can be used to regulate immune strength, and can be imparted with the indication: "Can be used to regulate immune strength". Here, the term "indication" includes not only indication on the container of, or in handling instructions for, a food or drink product, but also voice advertisements and written advertisements for food and drink products printed on paper media and on the web.

Further, the term "food and drink products imparted with the indication" means not just food and drink products imparted with indications on handling instructions or food and drink containers, but also refers to the case where an indication is not provided on handling instructions or the container, but a similar indication is provided by means of an advertisement such as a voice advertisement or a written advertisement for a food or drink product that is printed on a paper medium or the web. These indications include, for example, those that extol immune strength effects, such as "For people of weak constitution," "For nurturing strength," "For improving physical constitution," "For people prone to catching colds," "For people who are sensitive to seasonal changes," "For people who are sensitive to early spring," "For people with sensitive skin," "For taking examinations," and "For maintaining physical condition."

The composition of the present invention having the above immunoregulatory effects is formulated into the food and drink products of the present invention by established methods. The entity that consumes the food or drink product is not limited to human beings, and can be a pet such as a dog or cat, or any animal. That is, in the present invention, food and drink products also include animal feeds.

The food and drink products of the present invention are prepared by mixing active ingredients prepared from the fruit of the black currant to achieve immunoregulation such as the above improvement and fortification of immune strength. Food products can be in the form of solid foods, semiliquid foods such as creams, gelled foods, drinks, and the like. They can also be in the form of powders, granules, capsules, tablets, liquids, and the like.

The various components that are blended into food and drink products along with active ingredients prepared from the fruit of the black currant are not specifically limited; any of the various components that are normally employed can be used. Examples of such components are: glucose, fructose, sucrose, maltose, sorbitol, lactose, citric acid, tartaric acid, malic acid, succinic acid, lactic acid, casein, gelatin, pectin, agar, amino acids, pigments, fragrance materials, and preservatives.

Specific example of food products relating to the present invention are soft drinks, juices, jams, confections, and dairy products. The content of the effective ingredient prepared from the fruit of the black currant suitably falls within a range of 0.01 to 100 mg/g, but quantities exceeding this range can also be blended in.

The present invention is described in greater detail below through examples, but is not limited to the examples given below.

EXAMPLES

Example 1

Preparation of the Composition of the Present Invention from Isolated CAPS

CAPS were basically isolated according to Patent Document 1 and Nonpatent Document 8. The preparation will be briefly described below. A black currant puree was centrifuged to obtain black currant juice. This juice was passed at a rate of SV4 through a mixed bed column packed with equal quantities of cation exchange resin (Amberlite IR 120B HAG (made by Organo)) and anion exchange resin (IRA 410 OHAG (made by Organo)) and the fraction that passed through was recovered. The fraction obtained was passed through a Sep-Pak C18 Vac 35 mL (made by Millipore) to adsorb the polyphenol compounds onto solid phase resin, and the unadsorbed fraction was recovered. The fraction obtained was dialyzed with deionized water at 4° C. The fraction was then freeze-dried, yielding CAPS. In Patent Document 1, the CAPS are fractioned into polysaccharide A and polysaccharide B by precipitation from ethanol. However, in the present invention, the term "CAPS" refers to a mixture of polysaccharide A and polysaccharide B.

The CAPS thus obtained were dissolved in phosphate-buffered saline (PBS: phosphate-buffered saline produced by Difco (pH 7.4)). The pH was adjusted to 5.5 with 1 N hydrochloric acid. To this mixture was added β(beta)-galactosidase (made by Sigma Corp., derived from *Aspergillus oryzae*) to 0.1 w/v percent (8 units/mL). The mixture was incubated at 50° C. and sampled over time. The enzyme was deactivated by boiling for 10 minutes. The supernatant of each sample obtained by centrifugation was analyzed by HPLC gel filtration, and those samples with a composition containing polysaccharides of the present invention, the polysaccharide fraction of which (MW>1,000) had an average molecular weight of about 20,000, were identified.

The analysis column employed was a Shodex OHpak SB-804 (exclusion limit: MW 1,000,000). PBS was employed as equilibration buffer. The flow rate during analysis was 1 mL/min. A differential refractometer (RID) was employed as detector. Molecular weight markers in the form of T-2000 (MW 2,000,000), T-500 (MW 473,000), T-70 (MW 67,200), T-40 (MW 43,000), T-10 (MW 10,000) (all of which were made by Pharmacia), maltohexaose (MW 991), sucrose (MW 342), and glucose (MW 180) were employed.

A portion of the polysaccharides obtained at the time (average molecular weight of about 20,000) was subjected to molecular weight 1,000 ultrafiltration to remove the fraction with a low molecular weight of 1,000 or less (monosaccharides to oligosaccharides) and washed and removed, after which the composition of the neutral sugars was analyzed.

Further, the saccharides were dissolved to 4 mg/mL in PBS and the concentration of ethanol added was varied to examine the behavior of the active fraction. That is, ethanol was added to a variety of concentrations, the supernatant fraction and precipitate fraction were separated by centrifugation (10 minutes at 15,000 rpm), and PBS was added to the precipitate fraction to make the original volume and form a suspension. After evaporating off the ethanol from the supernatant fraction in a centrifugal evaporator, PBS as similarly added to make the original volume. The TNF-α(alpha) (a cytokine that is released primarily by macrophages) inducing activity of the supernatant fraction and precipitate fraction was measured at the various ethanol concentrations. Simultaneously, the various fractions were subjected to analysis by gel filtration HPLC.

The TNF-α(alpha)-inducing activity was measured by the following method. The mouse macrophage-like cell line RAW 264 was employed in the assay ($1 \times 10^5$ cells/mL, 100 microliters, 37° C., 5 percent $CO_2$ culture). The various fractions were added to the culture solution to achieve 40-fold dilutions, and the TNF-α(alpha) present in the supernatant after culturing overnight was measured with an ELISA quantification kit (Quantikine mouse TNF-α(alpha), made by R&D Systems) according to the accompanying manual.

FIG. 3 shows analysis chromatograms after 0 (undigested, predeactivated enzyme was boiled for 10 minutes after being added in prescribed quantities), 3, 8, and 35 hours, along with a calibration curve. The sample taken after 35 hours was completely digested by the enzyme. The average molecular weights of the polysaccharides produced after 3, 8, and 35 hours were 55,000, 19,000, and 2,400, respectively. That is, polysaccharides were produced in the sample digested for 8 hours. Molecules with molecular weights of 1,000 or lower (monosaccharides to oligosaccharides) were removed from the product containing these polysaccharides. The fraction obtained consisted solely of neutral sugars in the form of rhamnose, mannose, arabinose, galactose, xylose, and glucose in a component molar ratio of 18:3:19:30:1:29.

FIG. 4 shows the behavior of the active fraction in the ethanol aqueous solution. At ethanol concentrations of 30 percent and greater, the TNF-α(alpha)-inducing activity present in the supernatant diminished sharply. At ethanol concentrations of 40 percent and greater, the activity present in the supernatant almost disappeared. In HPLC analysis, almost no polysaccharides were detected in the supernatant at ethanol concentrations of 70 percent and above, but the activity did not fully migrate to the precipitate fraction.

Example 2

Preparation of the Composition of the Present Invention from Black Currant Puree (Juice)

Black current puree (made by SVZ) was incubated at various enzyme concentrations and temperatures. Sumilact L (a food-use enzyme comprised mainly of β(beta)-galactosidase, derived from *Aspergillus oryzae*, made by Shinnihon Kagaku Kogyo) was employed as the enzyme. Small quantities were sampled over time and boiled for 10 minutes to deactivate the enzyme. The centrifugation (15,000 rpm, 10 minutes) supernatant was analyzed by HPLC gel filtration and the viscosity thereof was measured. The analysis conditions during gel filtration were identical to those in Example 1. A Viscomate (model VM-1G-L, made by Yamaichi Electronics) was employed as viscometer.

The results are given in the table. The optimal temperature of β(beta)-galactosidase derived from *Aspergillus oryzae* is generally considered to be about 55° C. However, it became clear that conducting the reaction at about 40° C. was optimal for black currant (pH 2.9). This permitted the production of saccharides in the puree under mild conditions without losing the flavor of black currants. A approximately 1 percent (w/v) enzyme formulation (10,000 U/g) was suggested as being practical. When the reaction was conducted for 4 to 6 hours under these conditions, the average molecular weight of the CAPS contained in the puree decreased to in the vicinity of 20,000. This means that the present polysaccharides were produced. Reducing the viscosity to about ⅕ resulted in a physical property in the form of great ease of handling.

TABLE 1

| Sumilact L (% (w/v)) | Temperature (° C.) | Time (h) | Viscosity (cP) | Average molecular weight |
|---|---|---|---|---|
| 1 | 55 | 2 | 5.9 | — |
| 1 | 55 | 4 | 5.2 | — |
| 1 | 55 | 6 | 5.4 | — |
| 1 | 55 | 24 | 2.8 | 19,300 |
| 1 | 40 | 2 | 4.0 | — |
| 1 | 40 | 4 | 2.5 | 21,000 |
| 1 | 40 | 6 | 2.0 | 19,600 |
| 1 | 40 | 24 | 1.7 | 6,600 |
| Untreated puree (centrifugation supernatant after boiling) | | | 10.30 | >400,800 |
| Isolated CAPS (centrifugation supernatant after boiling) | | | | >235,653 |

As an example, a gel filtration chromatogram of the untreated puree when the reaction was conducted at 40° C. for 6 hours is shown in FIG. 5.

When the reaction was conducted with 1 percent (w/v) at 40° C., the CAPS in the puree were degraded after 24 hours to an average molecular weight of 6,600 despite the low pH of the black currant puree. Accordingly, conditions for deactivating the enzyme were then examined.

Black currant puree was treated under conditions of 0.9 percent (w/v) and 42° C. for 5 hours, after which small quantities were sampled, the reaction mixture was boiled for 10 minutes, and the centrifugation supernatant was recovered as a "sample after 5 hours of reaction." Simultaneously, separate sampling was conducted, the sample was divided into four equal portions, and the portions were incubated for 10 minutes in a water bath at 42 (positive control), 70, 75, and 80° C. Subsequently, the four equal portions were placed in a 42° C. water bath and incubated for another 19 hours (making a total of 24 hours from the start of the reaction). The samples were then boiled and centrifuged, and the supernatants were analyzed.

Analysis by HPLC gel filtration revealed that by maintaining the samples at least at a temperature of 70° C. or higher for 10 minutes, it was possible to deactivate the enzymatic activity within the black currant puree to a level that was not problematic. This deactivation operation also served to sterilize.

The results of Example 2 indicate that it was possible to obtain the composition of which chief ingredient is the polysaccharides of the present invention from puree without losing flavor under extremely mild enzymatic reaction conditions and under relatively mild deactivation and sterilization conditions.

Example 3

Measurement of Cytokine-Inducing Activity

CAPS obtained by the same method as in Example 1 were dissolved to 3 mg/mL (measurement value obtained by the phenol sulfuric acid method) in 50 mM sodium acetate (pH 5.5). To this, Sumilact L was added to 4 mg/mL and the mixture was reacted at 50° C. for one hour. The reaction solution was boiled at 100° C. for 3 minutes to deactivate the enzyme and centrifuged (12,000 rpm, 3 min) to obtain the supernatant. The average molecular weight of the polysaccharides contained in the supernatant obtained was estimated at about 30,000 to 31,000.

The supernatant was added to a 50-fold dilution to a culture solution of mouse abdomen macrophage. The abdomen macrophage was prepared by established methods. Specifically, thioglycolate medium was injected into the abdomen of an ICR mouse, the abdomen macrophages were recovered after four days, and, finally, the macrophages were adjusted to $1 \times 10^6$ cells/mL and seeded in a 96-well plate for use in the following test.

The TNF-α(alpha) present in the culture solution after culturing the macrophages overnight was measured with an ELISA quantification kit (Quantikine mouse TNF-α(alpha), made by R&D Systems) according to the accompanying manual.

The results are shown in FIG. 6. The composition of the present invention obtained by treating CAPS with β(beta)-galactosidase was found to have an in vitro cytokine-inducing activity of nearly ten times that of CAPS.

Example 4

Measurement of Antitumor Activity in Mice

The in vivo antitumor activity of the composition of which chief ingredient is polysaccharides of the present invention that was obtained in Example 1 was compared to that of several CAPS degradation products of varying average molecular weight.

Laboratory animals in the form of female ICR mice (SPF) purchased at the age of four weeks from Japan SLC and preliminarily reared for 8 days were employed in the experiments. The mice were reared in SPF animal rearing cages (8 to 18 hours of illumination, air replacement frequency of 18 times/hour) at a room temperature of 24±3° C. and a relative humidity of 55±15 percent during both the preliminary rearing period and the experimental period. The mice were kept five to a cage, sterilized distilled water was freely provided in a water bottle and solid feed (MF, Oriental Yeast) was freely provided in a mouse feeder. The individual mice were distinguished by the pigment (picric acid solution) application method.

An Ehrlich tumor cell strain that had been maintained (in ascitic form) for multiple generations in ICR mice was employed as the tumor cells that were transplanted into the mice. The ascites of the mice in which the tumor cells had been maintained for multiple generations in ascitic form was collected, diluted with sterile physiological saline, and used to prepare a free tumor cell solution with a concentration of $8 \times 10^6$ cells/mL. A 0.25 mL quantity of the free cell solution was transplanted subdermally into the inguinal region of each of the mice ($2 \times 10^6$ cells/mouse). The day the tumor cells were transplanted was denoted as day 0.

The preparation and dosages of the administration samples are given below.

In addition to the present polysaccharides obtained in Example 1, several CAPS degradation products of varying average molecular weight and undigested CAPS were diluted to 500-fold with PBS (polysaccharide concentration: 8 micrograms/mL each) to prepare administration samples. PBS was administered to the control group. Forced oral administration (10 mL/kg) was employed as the administration method.

The administration schedule is given below.

Denoting the day the tumor cells were transplanted as day 0, a single daily forced oral administration (10 mice per group) was conducted from day −6 to day 14. On the final day (day 14), the mice were dissected, and the tumors were excised and weighed with an electronic scale.

FIG. 7 shows the results of weighing the excised tumors. Only the present saccharides having an average molecular weight of about 20,000 produced a suppressing effect on tumor growth with a significant difference. Antitumor activity was low both back and forth.

Example 5

Mouse Antiallergy Test

The antiallergic activity of the composition of which chief ingredient is the present polysaccharides obtained in Example 1 was measured. A model of mouse allergy induced by egg white albumin was employed as the test system.

Laboratory animals in the form of 93 male BALB/c mice (SPF) purchased at the age of six weeks from Japan SLC and preliminarily reared for 1 day were employed in the experiments. The mice were reared in SPF animal rearing cages (7 to 19 hours of illumination, air replacement frequency of 18 times/hour) at a room temperature of 24±3° C. and a relative humidity of 55±15 percent during both the preliminary rearing period and the experimental period. The mice were kept five to a cage, sterilized distilled water was freely provided in a water bottle, and solid feed (MF, Oriental Yeast) was freely provided in a mouse feeder. The individual mice were distinguished by applying picric acid to their fur.

The preparation and dosages of the administration samples are given below.

The administration samples were prepared by the method described in Example 1. The average molecular weights of the administration samples employed in the present embodiment were MW 59,000, MW 24,000, and MM 3,500. Undigested CAPS included, the administration samples were obtained by diluting a partially degraded reaction solution 10-fold (polysaccharide concentration: 400 micrograms/mL). Cycloformamide (30 mg/kg, 3 mg/mL, and 0.5 percent CMC suspension) was employed as a positive control.

The administration schedule is given below.

Each day from day 15 to day 21 (with the initial immunization day being denoted as day 0), the above administration samples were forcefully administered orally with an oral sonde for mice. The dosage was 0.1 mL per 10 g of mouse body weight.

Preparation of the Sensitizing Antigen

Egg white albumin (OVA, made by Seikagaku Corporation) was employed as the sensitizing antigen. For primary immunization, a suitable quantity of OVA was weighed out and dissolved in physiological saline to prepare a 66 microgram/mL solution. A 10 mL quantity of the OVA solution and 10 mL of aluminum hydroxide gel (Al(OH)$_3$, 13 mg/mL, A8222 made by Sigma) were thoroughly mixed with ice cooling to prepare a suspension comprising a 33 microgram/mL concentration of OVA and a 6.5 mg/mL concentration of Al(OH)$_3$. For secondary immunization, a suitable quantity of OVA was weighed out and dissolved in physiological saline to prepare a 25 mg/mL solution.

The allergy-inducing method is described below.

A 0.3 mL quantity of primary immunization antigen was administered twice into the abdominal cavities of six-week-old mice, on day 0 and day 4. Secondary immunization antigen solution was placed in a centrifugation tube and dipped for 3 seconds into the noses of the mice to conduct nasal sensitization. Nasal sensitization was conducted three times daily on days 9 to 13.

The group composition is given below.

The groups were constituted as shown in Table 2 so that there was no difference in the OVA-specific IgE levels in plasma collected on day 14. There were 6 to 12 animals per group (based on OVA-IgE measurement results).

TABLE 2

| Group No. | Test group | No. of mice |
|---|---|---|
| 1 | Control (sensitization) | 10 |
| 2 | Undigested CAPS | 12 |
| 3 | Enzyme-treated CAPS (MW 59,000) | 10 |
| 4 | Enzyme-treated CAPS (MW 24,000) | 10 |
| 5 | Enzyme-treated CAPS (MW 3,500) | 10 |
| 6 | Cyclophosphamide 30 mg/kg | 6 |
| 7 | Normal mice (unsensitized) | 7 |

The items examined are described below.

Body weight was determined with a scale on days 0, 7, 14, and 22. General symptoms were observed daily from day 0 to day 22. Blood plasma analysis was conducted by measuring the OVA-specific IgE level using plasma obtained by centrifuging blood drawn from the ophthalmic vein on days 0, 14, 18, and 22.

The method of quantifying the OVA-specific IgE is described below.

Biotinylation of OVA:

OVA (made by Seikagaku Corporation) was biotinylated with an Immunoprobe Biotinylation Kit (the BK-101, made by Sigma-Aldrich).

The method employed was in accordance with the use manual.

Detection of OVA-Specific IgE Antibody in Mouse Blood Plasma by ELISA:

The following ELISA detection system was established to determine the OVA-IgE titer. Goat anti-mouse IgE antibody (made by Bethyl) was diluted to 10 micrograms/mL with PBS, applied 100 microliters/well on a microplate (Nunk), and left standing overnight at 4° C. The microplate coated with IgE antibody was washed three times with PBS, 200 microliters/well of 0.5 percent casein-PBS solution was added, the microplate was left standing for three hours at room temperature to conduct blocking. The microplate was again washed three times with PBS, 100 microliters of mouse plasma sample diluted 20-fold with 0.5 percent casein-PBS were added to each well, and the microplate was left standing overnight at 4° C. to allow the reaction to take place. Washing was conducted four times with PBS, biotinylated OVA diluted with casein (10 microgram/mL) was added to each well, and the reaction was conducted for 2 hours at room temperature. Washing was conducted 5 times with PBS, 100 microliters of streptavidin-peroxidase (S-5512, made by Sigma) diluted with casein (0.5 microgram/mL) was added, and the microplate was left standing for 1 hour at room temperature. Washing was conducted five times with 0.1 percent Tween-PBS and 100 microliters of a color-forming solution (ABTS Peroxidase Substrate System, made by Cappelle) were added. The microplate was left standing for from 1 to 3 hours, the absorbance at wavelengths of 405 nm and 492 nm was measured with a microplate reader, and the value from the former was subtracted from the value from the latter. The plasma of an individual exhibiting a high plasma OVA-specific IgE value was stored at −80° C., this was adopted as a positive control in preparing a dilution series, and a calibration curve was plotted. The OVA-specific IgE value was then denoted as the activity relative to the calibration curve.

FIG. 8 gives the results of measurement of the OVA-specific IgE level in blood (plasma) collected on the final day (day 22). CAPS degradation product with an average molecular weight of about 20,000, that is, just the present polysaccharides, exhibited a tendency to inhibit an increase in IgE.

FIG. 9 shows change in body weights. The administration of cyclophosphamide, a strong immunosuppressant, produced a side effect in the form of a reduction in the body weight of the mice. The present saccharides produced no effect whatsoever. These results indicated that the present saccharides were highly safe.

Example 6

Human Hay Fever Intervention Test

The suppressive effect on cedar pollen allergy symptoms in humans and safety of the composition of which chief ingredient is polysaccharides derived from the juice of the black currant of the present invention were examined.

The test was conducted as a comparison of double-blind test groups comprised of a test product group and a placebo group. The test method is set forth below.

Twenty-eight men and women aged 20 to 65 who were positive for cedar pollen-specific IgE (FEIA method) and who had presented with symptoms of nonseasonal allergic rhinitis for the past two years ranging in severity from light to severe were asked to take six test products from the examples (amounting to about 360 mg of polysaccharides derived from black currant juice) and six placebos for about four weeks prior to the scatter of cedar pollen to four weeks after the start of scatter, or a total of eight weeks.

The quantity of cedar pollen scattered began to increase in late February, peaking in the fifth to sixth weeks (Mar. 8 to 14, 2006). Prior to taking the test products, after having taken the test products for 4 weeks, and after having taken them for 8 weeks, participants were seen by the physician in charge of the test, who provided an opinion (on swelling of the inferior turbinate mucosa) and collected blood. Prior to and following the conclusion of the consumption of the test products, a QOL survey was conducted on subjective symptoms using a standard Japanese allergic rhinitis survey form. Various items were measured in the blood that was collected, such as total proteins, albumin, alkali phosphatase (ALP), glutamate oxaloacetate transferase (GOT), glutamate pyruvate transaminase (GPT), lactate dehydrogenase (LDH), γ(gamma)-glutamyl transpeptidase (γ(gamma)-GTP), cholinesterase, total bilirubin (T-BIL), direct bilirubin (D-BIL), indirect bilirubin (I-BIL), creatine phosphokinase (CPK), total cholesterol, neutral fats, urea nitrogen, creatine, uric acid, and specific IgE antibody (antigen: cedar).

The method of producing the test products is set forth below.

As indicated in Example 2, a black currant puree was subjected to enzymatic treatment (the addition of 10,000 U/g of Sumilact L to a final concentration of 0.9 percent (w/v) and reaction at 42° C. for 5 hours), after which the enzyme was deactivated at 70° C. for 10 minutes. Next, the supernatant was recovered by centrifugation, dextrin was added to the supernatant comprised principally of polysaccharides (CAPS) of the present invention that had been obtained, and the mixture was freeze-dried. The dried product (with a dextrin content of 49.2 percent (w/w)) was pulverized, and powdered fragrance material in the form of black currant micron M-10759 (made by Takasago International Corporation) was admixed to 0.6 percent (w/w), yielding a tablet-making powder. This tablet-making powder was used to form tablets, yielding chewable tablets weighting 2 g each.

The method of producing a placebo indistinguishable from the test product is set forth below.

An 800 g quantity of dextrin, 108 g of granulated sugar, 50 g of citric anhydride, 36 g of Sun Red No. 5 (made by San-Ei Gen F.F.I.), and 6 g of black currant micron (made by Takasago International Corporation) were admixed to obtain a tablet-making powder. This tablet-making powder was used to form tablets, yielding chewable tablets weighting 2 g each.

A total of 28 test subjects were organized into a test product group and a placebo group, each comprised of 14 persons. All symptoms presented by the test subjects were then evaluated for safety.

In validity evaluation, among test subjects who were ranked from class 1 to 5 based on an IgE antibody examination (RAST value) prior to taking the test product, a total of four cases in the test product group deviated from the test for consumption rate violations where the amount of test product not consumed reached the equivalent of 10 percent of the total number of days of consumption or for combined drug-use violations where a drug that could potentially affect evaluation was continuously taken. A total of four cases in the placebo group deviated from the test by quitting part way through, committing consumption rate violations, or committing combined drug-use violations. These cases were excluded from analysis, so that in the end, analysis was conducted for 10 test subjects in the test product group and 9 test subjects in the placebo group.

The results of the validity evaluation are given below:

1) Physician's Opinion (on Swelling of the Inferior Turbinate Mucosa)

The degree of swelling of the inferior turbinate mucosa was scored prior to consumption of the test product, four weeks after the start of consumption, and eight weeks after, and the mean value±one standard deviation was calculated for each period for the test product group and the placebo group. When the change in scores within each group was compared for the period before consumption of the test product, four weeks after the start of consumption, and eight weeks after, a significant ($p<0.05$) deterioration in score was found for the placebo group and no significant change was found for the test product group (FIG. 10). Although a comparison of the change prior to consumption of the test product and eight weeks after in the test product group and the placebo group did not reveal a significant difference (test product group vs. placebo group, $p=0.0572$), the test product group was lower than the placebo group and a tendency to suppress symptoms by consumption of the test product was found.

2) Specific IgE Antibody Examination (Antigen: Cedar)

The specific IgE antibody value was measured prior to consumption of the test product, four weeks after the start of consumption, and eight weeks after. A comparison of the average antibody value of the test product group and the placebo group revealed no difference between the test product group and the placebo group in antibody value prior to consumption of the test value, four weeks after, or eight weeks after.

3) QOL Survey (Japanese Allergic Rhinitis Survey Form)

In QOL surveys conducted prior to the start of consumption of the test product and after consumption had ended, scores were assigned to the degrees of items relating to the nose and eyes in the test product group and placebo group, the mean value±one standard deviation was calculated for each period, and comparisons were made between groups and within groups. A comparison by period of the scores assigned to items between groups for the period prior to the start of consumption of the test product and after consumption had ended for the test product group and the placebo group revealed a significant difference (p<0.05) between the two groups in the item "Eye itchiness" after eight weeks, with a decrease in symptoms in the test product group. An intergroup comparison of the change in the score prior to consumption of the test product and after eight weeks in the test product group and the placebo group revealed a tendency for the change in the test product group in "Sneezing" and "Tearing" to be slightly smaller than that in the placebo group (p=0.0809, p=0.0563), with a significant decrease (p<0.05) in "Eye itchiness" (FIG. 11). These results revealed worse "Sneezing," "Eye itchiness," and "Tearing" caused by pollen in the placebo group than in the test product group.

Safety Evaluation

In this test, no side-effects or abnormal variation in clinical examination results attributed to the test product were observed; the test products were thought to be free of safety problems.

The composition of which chief ingredient is polysaccharides (CAPS) derived from black currant juice of the present invention had the effect of improving or preventing "Eye itchiness," which is the main symptom of cedar pollen symptoms, and was found to tend to improve nose symptoms in the form of swelling of the inferior turbinate mucosa and "Sneezing," as well as eye symptoms in the form of "Tearing." This suggested that an alleviating effect could be expected on cedar hay fever, which causes allergy symptoms. Further, since no side-effects were observed, long-term consumption in peace was possible.

INDUSTRIAL APPLICABILITY

The novel composition of the present invention, of which chief ingredient is polysaccharides that can be obtained by definitive partial degradation with specific enzymes of the polysaccharide fraction contained in black currant juice, is useful in the fields of food and drink products and pharmaceutical products.

Figure 1:
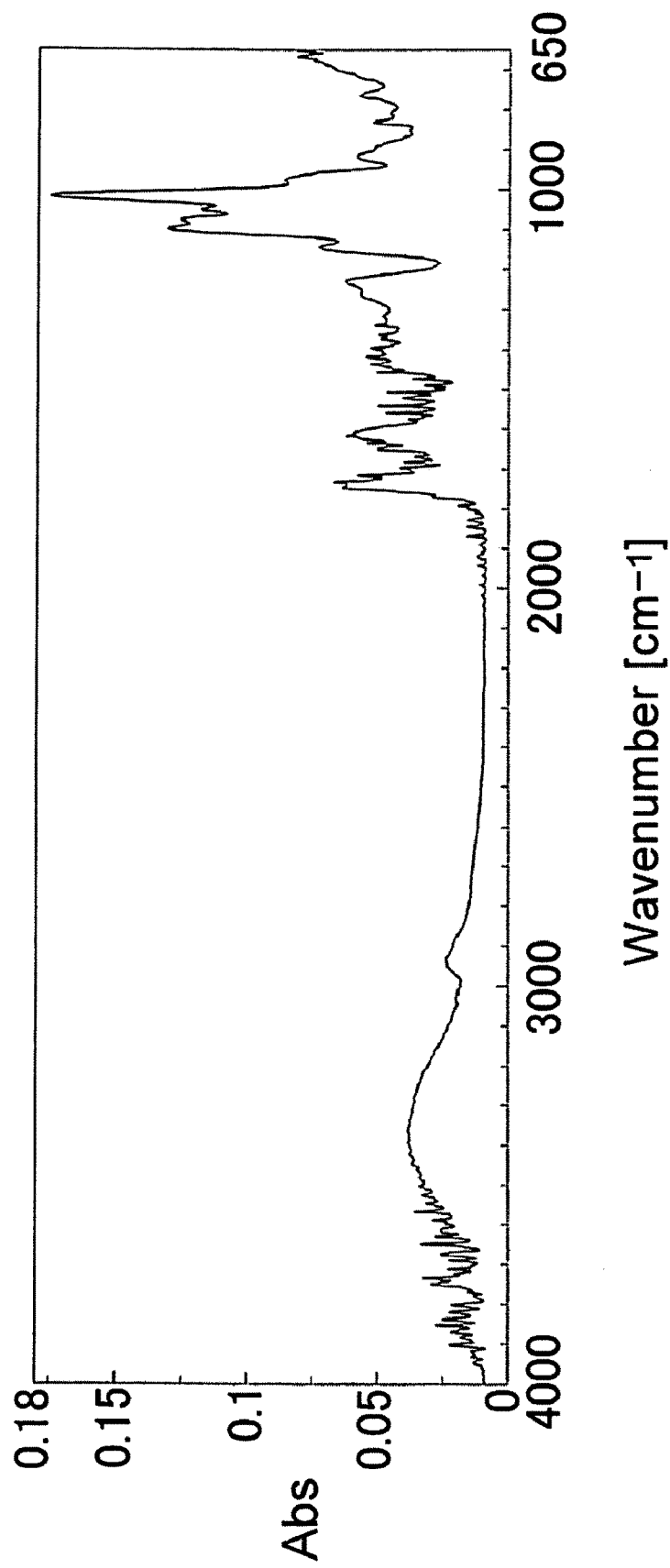
FIG. 1 Shows an infrared radiation absorption spectrum of the composition of the present invention.
Figure 2:
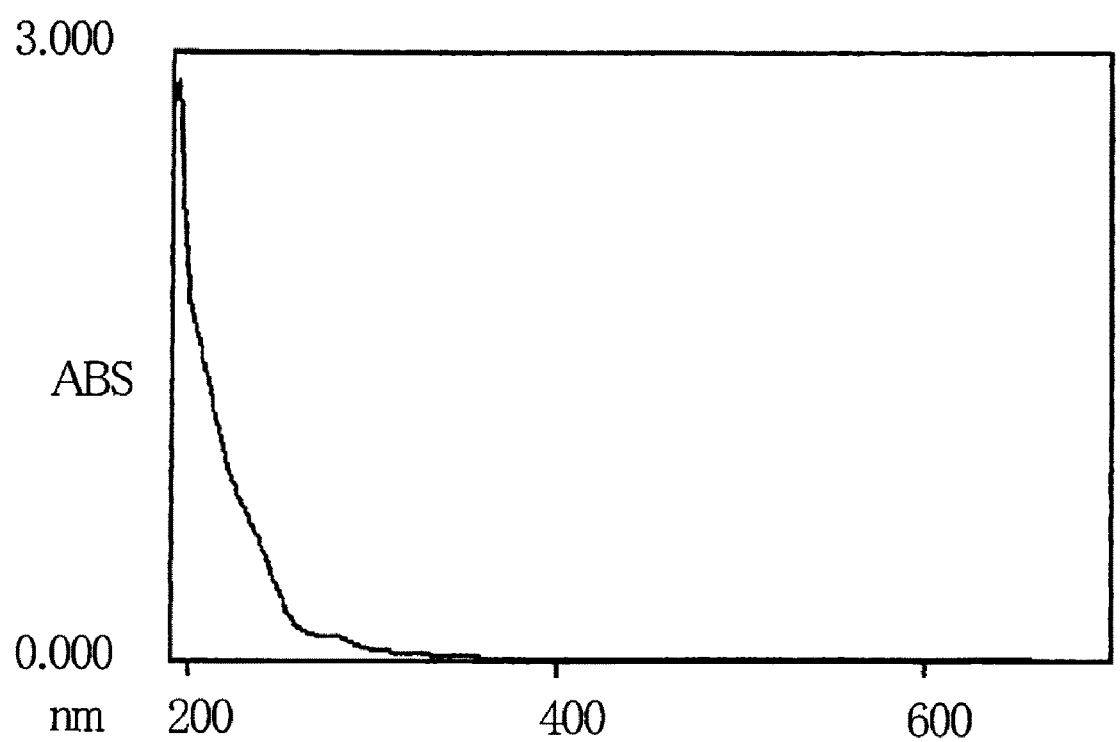
FIG. 2 Shows an absorption spectrum of the composition of the present invention.
Figure 3:
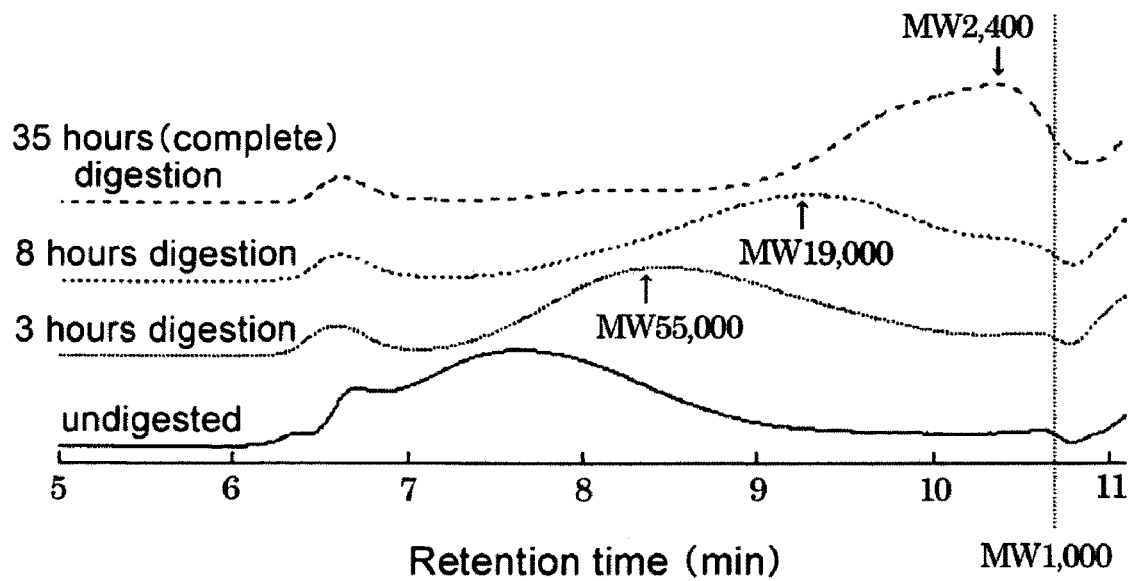
FIG. 3 Shows a gel filtration chromatogram of the polysaccharides contained in the composition of the present invention and the plot of a calibration curve.
Figure 3:
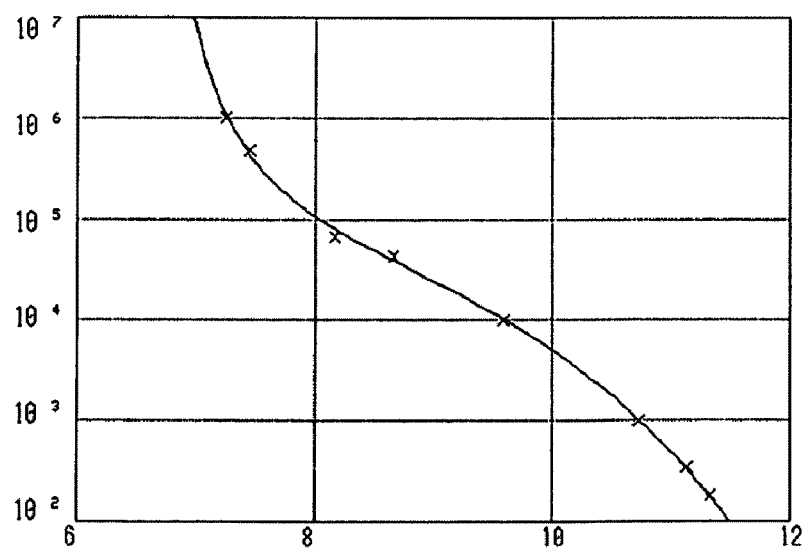
Figure 4:
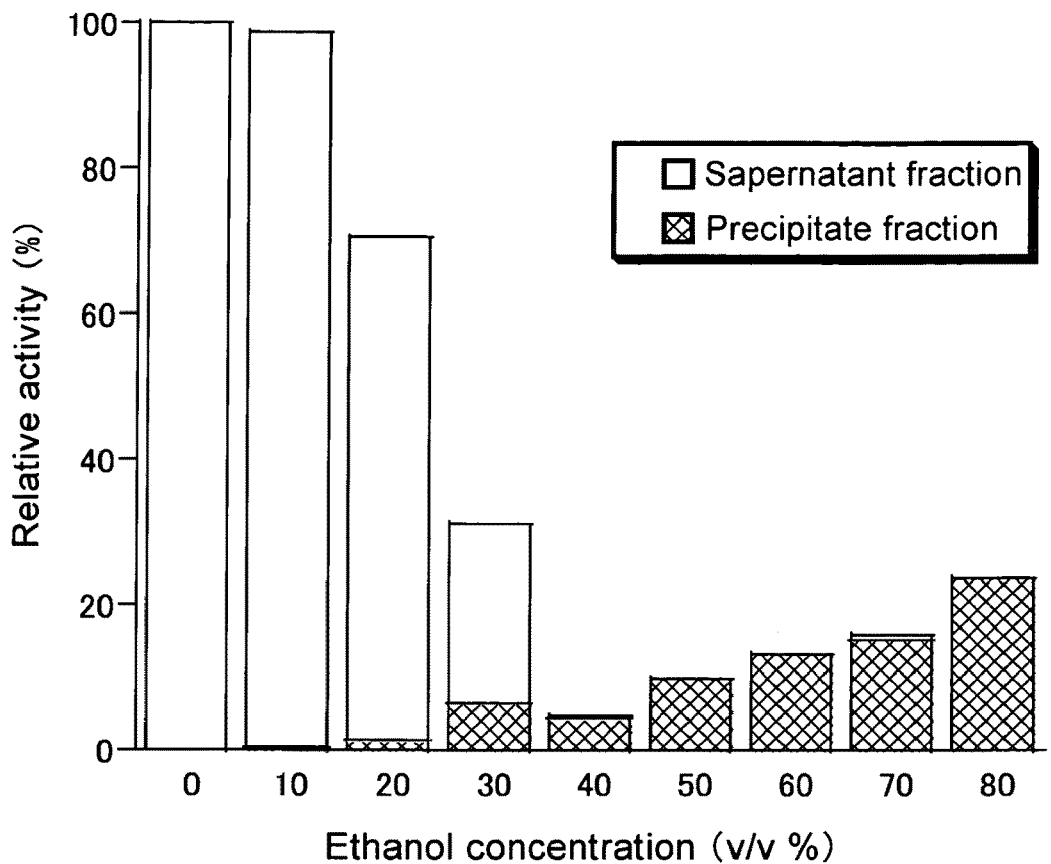
FIG. 4 Shows the activity of the polysaccharides contained in the composition of the present invention in an ethanol aqueous solution.
Figure 5:
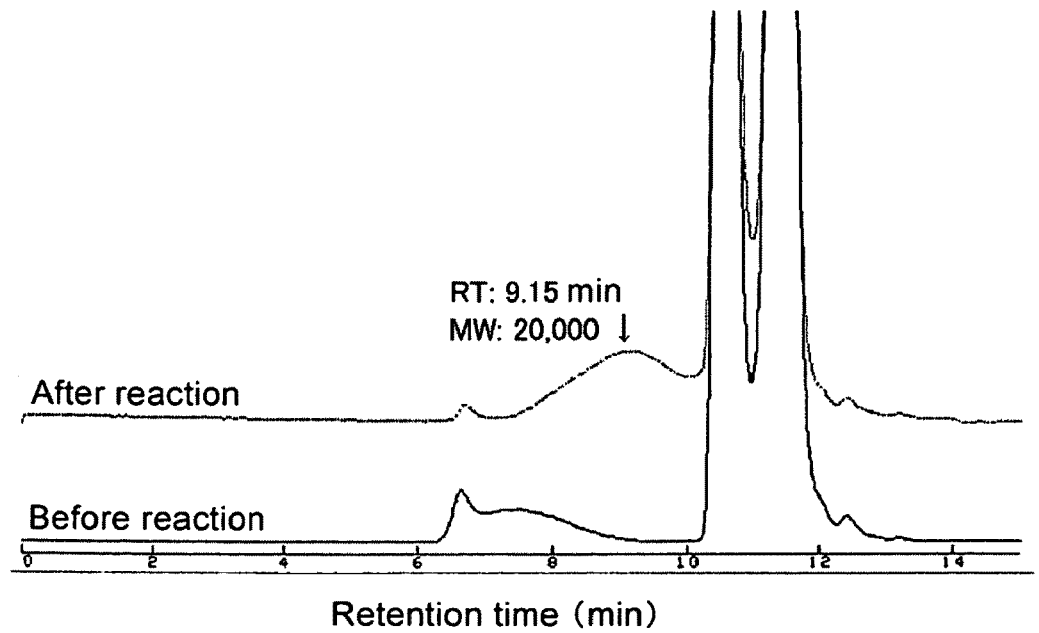
FIG. 5 Shows gel filtration chromatograms of black currant puree before and after enzyme treatment in Example 2.
Figure 6:
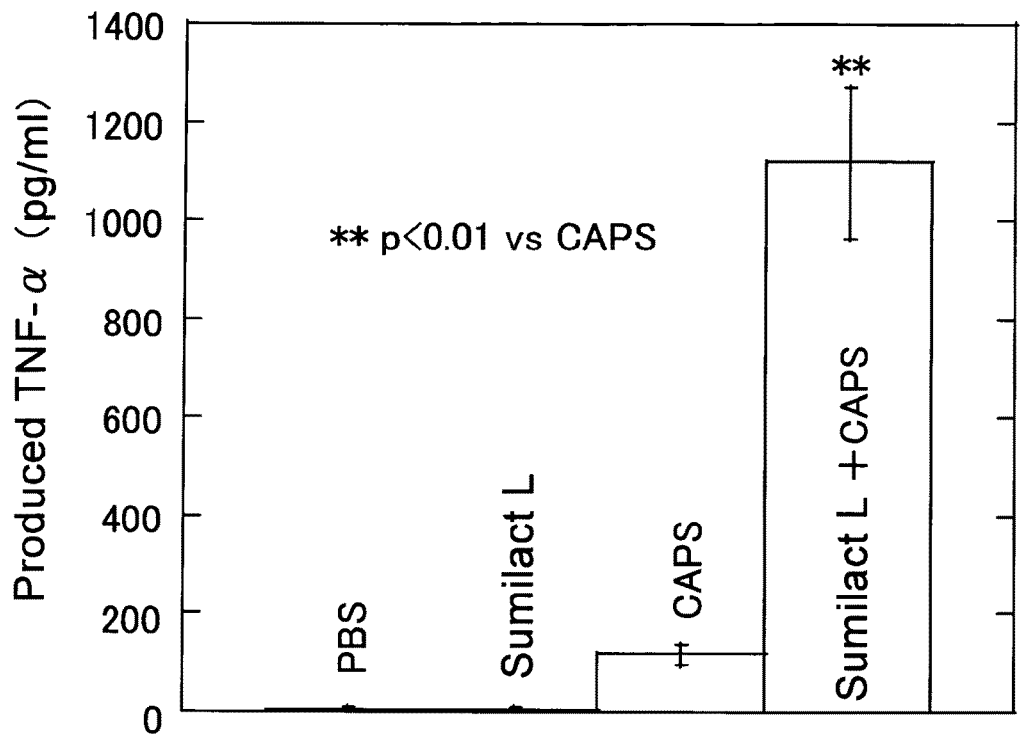
FIG. 6 Shows the results of measurement of cytokine-inducing activity in Example 3.
Figure 7:
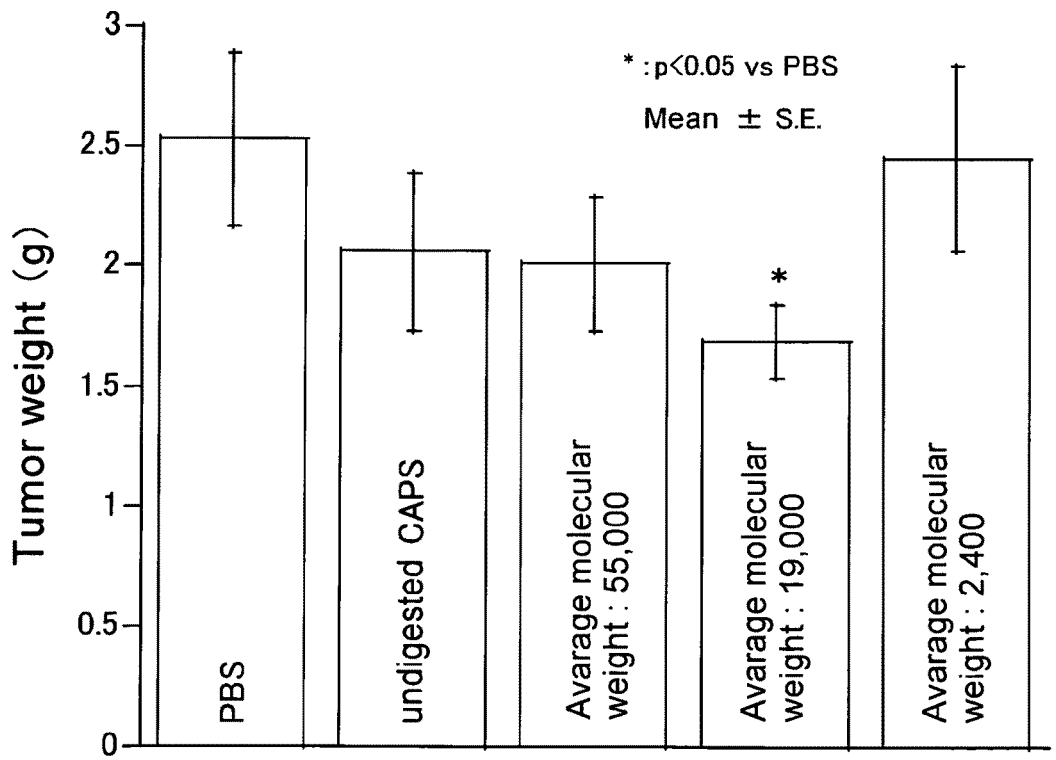
FIG. 7 Shows the mouse antitumor effect of the composition of the present invention in Example 4.
Figure 8:
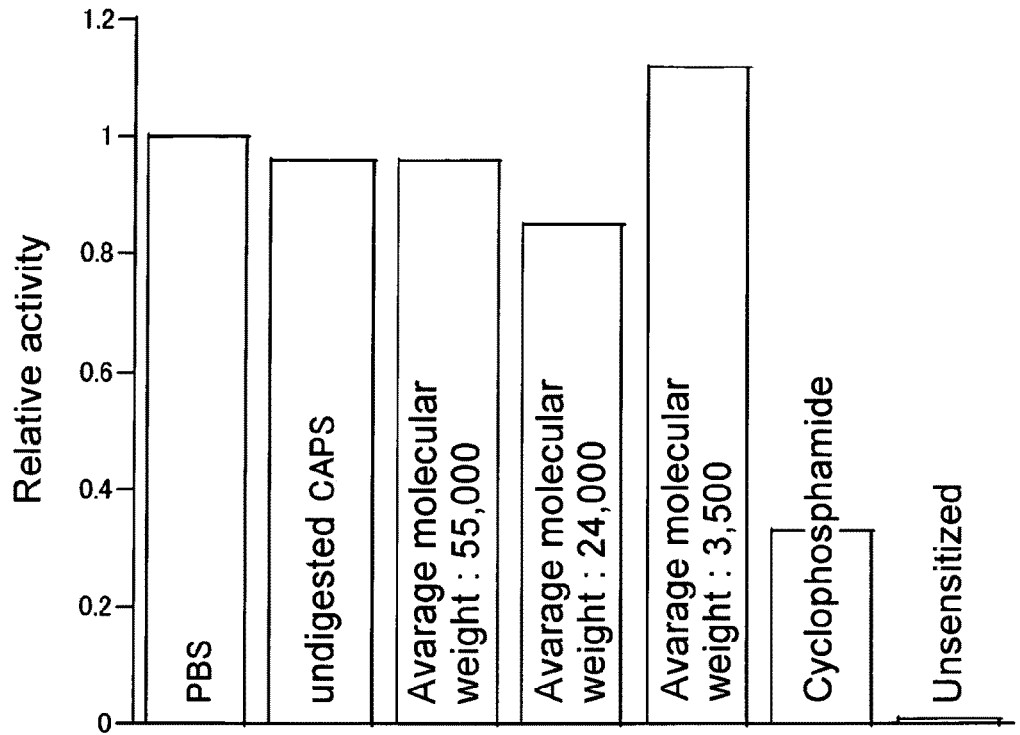
FIG. 8 Shows the antiallergic effect of the composition of the present invention in Example 5.
Figure 9:
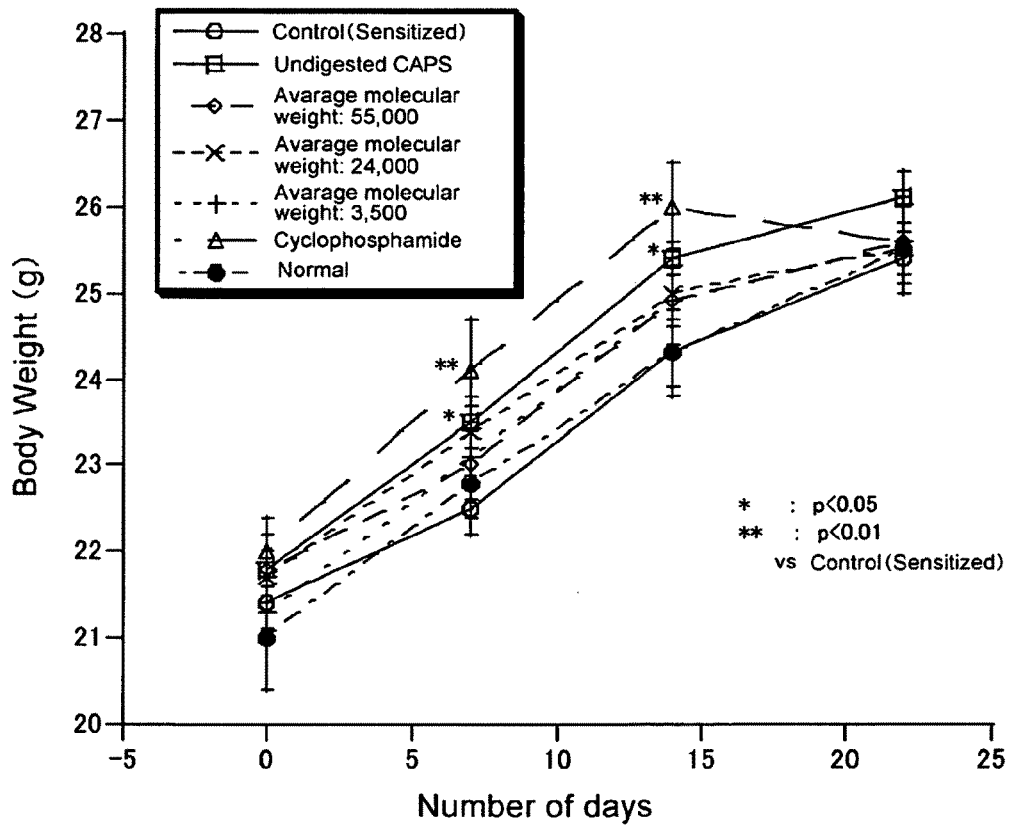
FIG. 9 Shows the change in body weights of mice to which the composition of the present invention was administered in an antiallergy test in Example 5.
Figure 10:
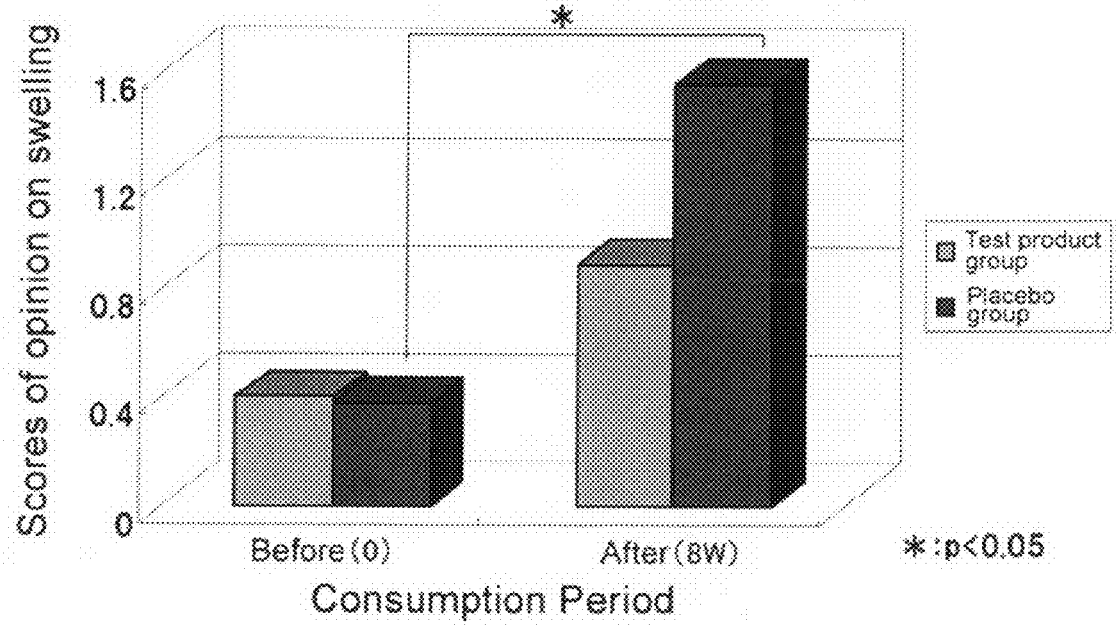
FIG. 10 Shows variation in the scores of a physician opinion on nasal cavity swelling before and after consumption of the test food product in a hay fever intervention test in humans in Example 6.
Figure 11:
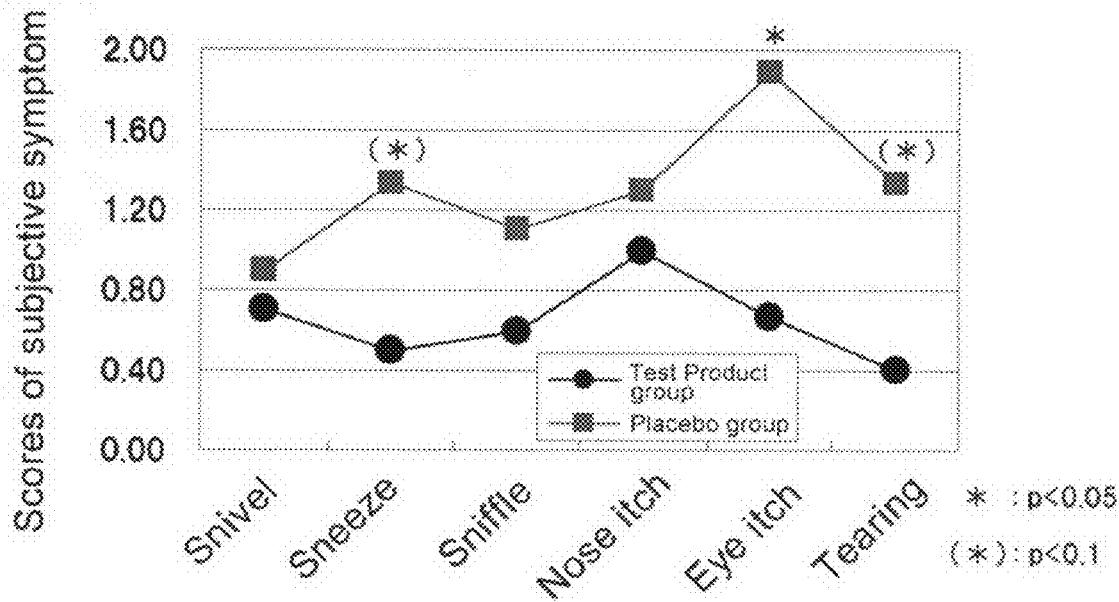
FIG. 11 Shows variation in QOL scores for various symptoms before and after consumption of the test food product in a hay fever intervention test in humans in Example 6.

The invention claimed is:

1. A composition comprising an immunoregulatory functional effective amount of polysaccharides having an average molecular weight of 10,000 to 40,000, the neutral sugars of rhamnose, mannose, arabinose, galactose, xylose, and glucose and wherein a molar ratio of the rhamnose:mannose:arabinose:galactose:xylose:glucose in a fraction having a molecular weight of 1,000 or greater is 18:3:19:30:1:29, and wherein said composition is obtained from black currant juice which has been partially digested by beta-galactosidase.

2. The composition of claim 1, further being readily soluble in water and in 0 to 20% (v/v) ethanol aqueous solutions.

3. The composition of claim 1, wherein the average molecular weight of said polysaccharides is about 20,000.

4. The composition of claim 1, wherein rhamnose, mannose, arabinose, galactose, xylose, and glucose are the only neutral sugars.

5. The composition of claim 1, further comprising protein and a polyphenol compound.

6. A method of making the composition of claim 1, wherein the polysaccharides of claim 1 are obtained from black currant juice which has been partially digested by beta-galactosidase.

7. An immunoregulator comprising the composition obtained by the method of claim 6.

8. The immunoregulator of claim 7, having an antitumor effect and/or an antiallergic effect.

9. The immunoregulator of claim 7, having a hay fever-suppressing effect.

10. A beverage or food comprising the composition obtained by the method of claim 6.

11. An immunoregulator comprising the composition of claim 1.

12. A beverage or food comprising the composition of claim 1.

* * * * *

UNITED STATES PATENT AND TRADEMARK OFFICE
CERTIFICATE OF CORRECTION

| | | |
|---|---|---|
| PATENT NO. | : 7,879,370 B2 | Page 1 of 1 |
| APPLICATION NO. | : 12/226671 | |
| DATED | : February 1, 2011 | |
| INVENTOR(S) | : Ryoji Takata et al. | |

It is certified that error appears in the above-identified patent and that said Letters Patent is hereby corrected as shown below:

"(22) PCT Filed: April 4, 2007" should be corrected to read --(22) PCT Filed: April 20, 2007--

Signed and Sealed this
Seventeenth Day of May, 2011

David J. Kappos
*Director of the United States Patent and Trademark Office*